(12) United States Patent
Hamidi et al.

(10) Patent No.: US 7,582,459 B2
(45) Date of Patent: Sep. 1, 2009

(54) PROCESS FOR PRODUCING A CAPSULAR POLYSACCHARIDE FOR USE IN CONJUGATE VACCINES

(75) Inventors: Ahd Hamidi, The Hague (NL); Michel Francois Beurret, De Bilt (NL)

(73) Assignee: De Staat der Nederlanden, vert. door de minister van VWS, The Hague (NL)

( * ) Notice: Subject to any disclaimer, the term of this patent is extended or adjusted under 35 U.S.C. 154(b) by 0 days.

(21) Appl. No.: 10/571,600

(22) PCT Filed: Sep. 10, 2004

(86) PCT No.: PCT/NL2004/000627

§ 371 (c)(1),
(2), (4) Date: Jul. 5, 2006

(87) PCT Pub. No.: WO2005/024038

PCT Pub. Date: Mar. 17, 2005

(65) Prior Publication Data

US 2007/0065460 A1 Mar. 22, 2007

(30) Foreign Application Priority Data

Sep. 11, 2003 (EP) .................................. 03077881

(51) Int. Cl.
*C12P 19/28* (2006.01)
(52) U.S. Cl. ........................................ 435/170; 435/41
(58) Field of Classification Search .................. 435/85.1
See application file for complete search history.

(56) References Cited

U.S. PATENT DOCUMENTS

| | | | | |
|---|---|---|---|---|
| 4,220,717 | A * | 9/1980 | Kuo | ............................ 435/101 |
| 4,242,501 | A * | 12/1980 | Cano et al. | .................. 536/127 |
| 4,644,059 | A | 2/1987 | Gordon | |
| 5,192,540 | A | 3/1993 | Bristol et al. | |
| 5,316,926 | A * | 5/1994 | Brown et al. | .................. 435/101 |
| 5,563,051 | A * | 10/1996 | Ellwood et al. | .............. 435/101 |
| 6,410,025 | B1 * | 6/2002 | Lander | ...................... 424/193.1 |
| 6,891,037 | B1 * | 5/2005 | Hasler et al. | .................. 536/127 |

FOREIGN PATENT DOCUMENTS

EP 0 024 493 3/1981

OTHER PUBLICATIONS

Peeters Carla C A M et al: "Preparation of polysacchardie-conjugate vaccines.", Methods in Molecular Medicine. 2003, vol. 87. Aug. 2003, pp. 153-174, XP001204262, ISSN: 1543-1894, the whole document.

Merritt J et al:, Development and scale-up of a fed-batch process for the production of capsular polysaccharide from haemophilus influenzae, Journal of Biotechnology, Elsevier Science Publishers, Amsterdam, NL, vol. 81, No. 2-3, Aug. 25, 2000 pp. 189-197, XP004210490, ISSN: 0168-1656, the whole document.

* cited by examiner

*Primary Examiner*—Robert A Zeman
*Assistant Examiner*—Nina A. Archie
(74) *Attorney, Agent, or Firm*—Young & Thompson

(57) ABSTRACT

A method for producing a polysaccharide and a conjugate vaccine including the polysaccharide produced according to the method. A characteristic step in the method is that the pH of the culture medium is kept at a constant value with base or acid until adjustment with respectively base or acid is not possible anymore. Using the method, capsular polysaccharide may be obtained in a high yield in a relatively short time. The method is straightforward, reproducible and cost-effective.

9 Claims, 2 Drawing Sheets

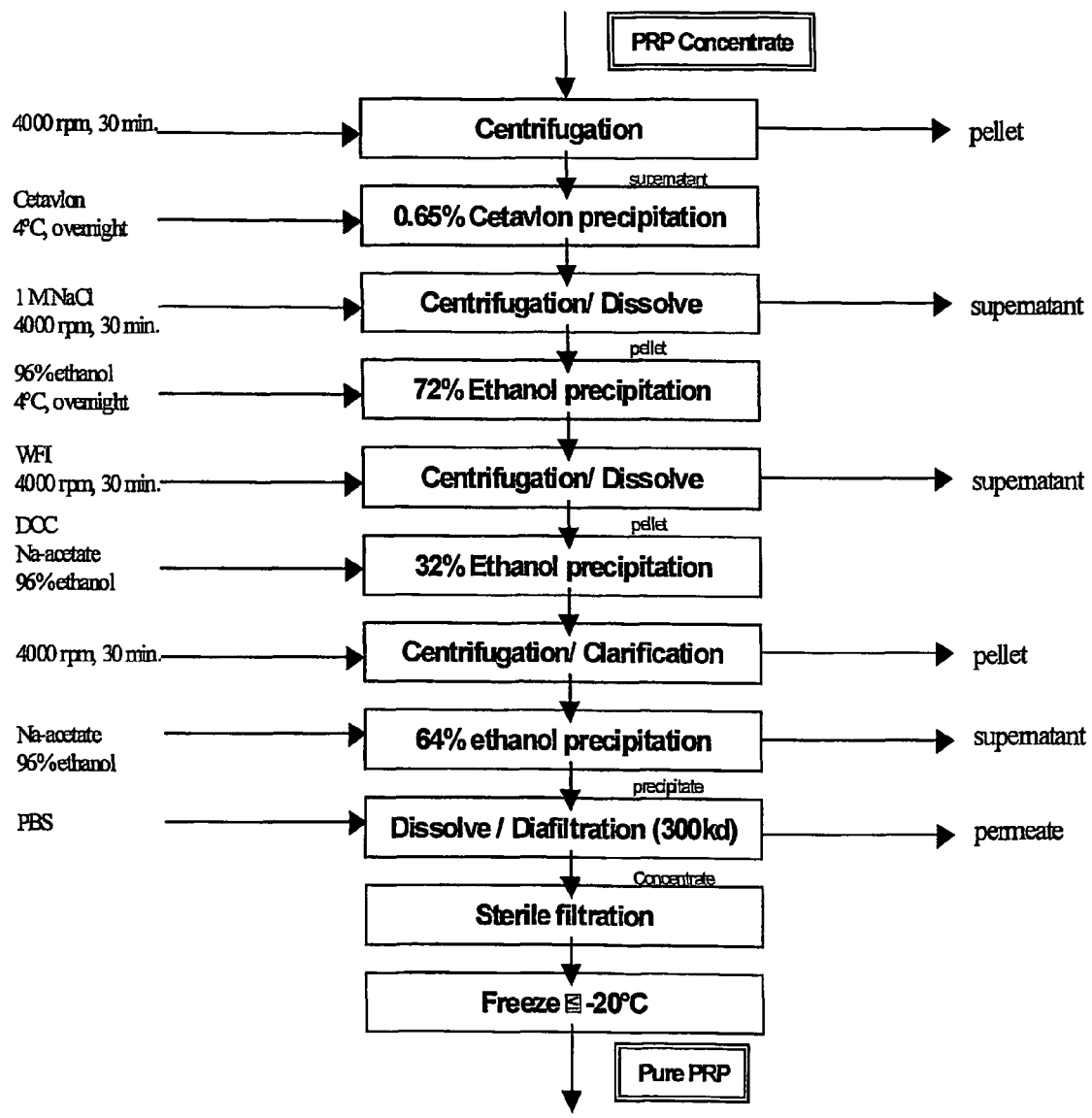

PROCESS FOR PRODUCING A CAPSULAR POLYSACCHARIDE FOR USE IN CONJUGATE VACCINES

BACKGROUND OF THE INVENTION

1 Field of the Invention

Figure 1:
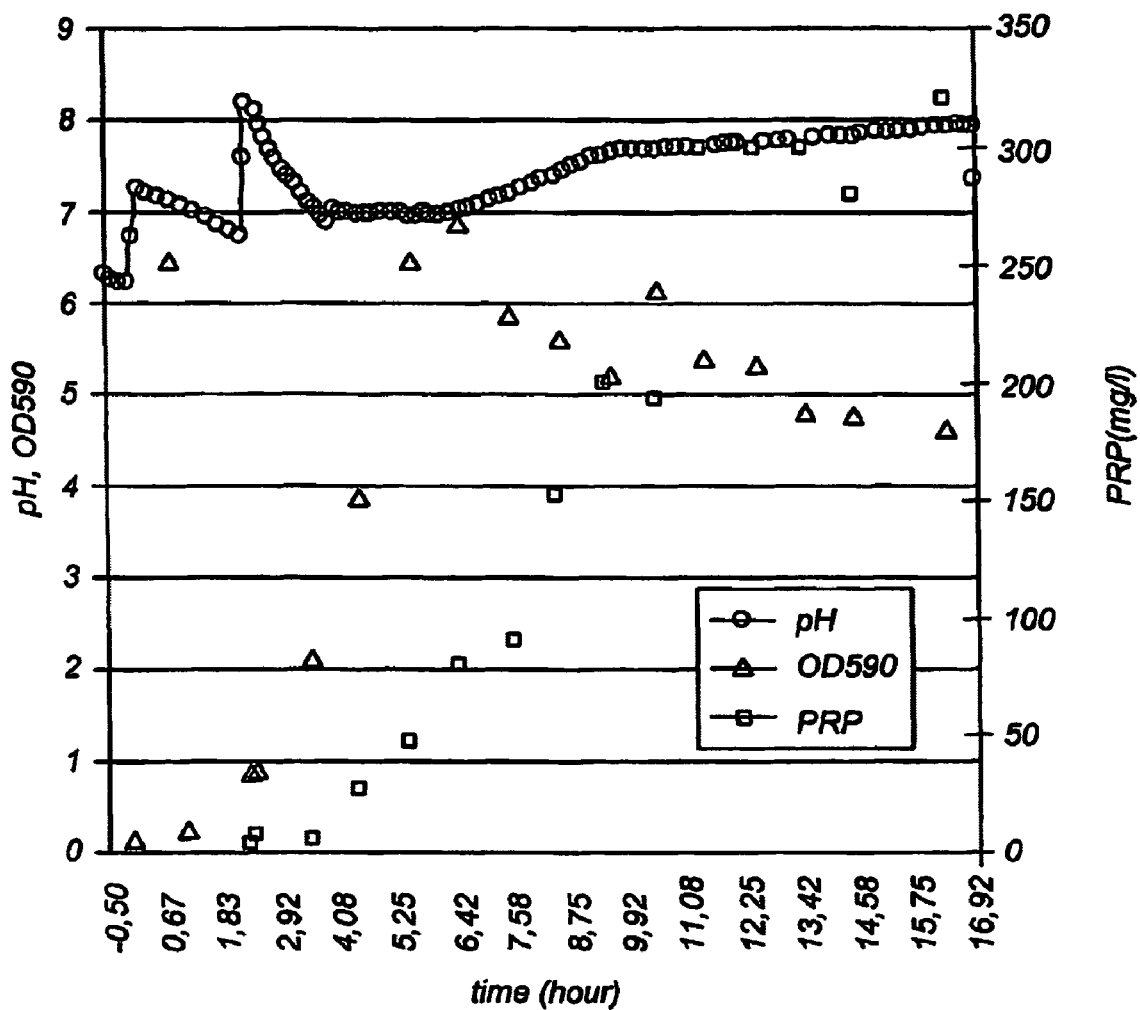

The present invention relates to the production of bacterial capsular polysaccharides and their use for the production of conjugate vaccines.

2 Description of the Related Art

The first step in making a vaccine is to separate the disease-making, from the immune-inducing activity. In practice this means isolating or creating an organism, or part of one, that is unable to cause full-blown disease, but that still retains the antigens responsible for inducing the host's immune response.

We distinguish two major groups of vaccines: whole organism vaccines and sub-unit vaccines. Whole organism vaccines are produced by killing/inactivating or attenuating/weakening organisms. Sub-unit vaccines include vaccines based on for example protein antigens and carbohydrate antigens.

Anti-bacterial vaccines produced using carbohydrate antigens may be composed of a purified (capsular) polysaccharide from the disease-causing organism. Examples of such vaccines are: *Haemophilus influenzae* type b (Hib), *Neisseria meningitidis* (A, C, W and Y), *Salmonella typhi* (Vi), and *Streptococcus pneumoniae* (23 different serotypes) polysaccharide vaccines.

Polysaccharide vaccines appeared not to protect infants under 2 years of age and not to induce long term T-cell memory. Therefore, a new generation of conjugated polysaccharide vaccines was introduced. Conjugate vaccines appeared to be immunogenic in young children and induce a long-term memory. Conjugate vaccines are mainly produced by attaching the polysaccharide to a protein carrier.

The first conjugate vaccine that was introduced worldwide was directed against *Haemophilus influenzae* type b (Hib). *Haemophilus influenzae* type b causes pneumonia and meningitis, mostly in young children.

It spreads by droplet through coughs, sneezing and in overcrowded living conditions. It is estimated to cause 2 to 3 million cases of disease each year and about 450,000 deaths, the vast majority of them in developing countries.

Several vaccines against Hib are already in widespread use in high-income countries, where they have virtually wiped out the disease. The vaccines are among the safest now in use. Studies have confirmed the effectiveness of these vaccines in low-income countries, but relatively few of them have begun routine use in infants. Hib vaccine is one of the most under-utilized vaccines because of its relatively high cost in comparison with the vaccines routinely used in the regular childhood immunization program.

The production processes used nowadays are relatively expensive, and include a long cultivation step of about 16-18 hours, see e.g. U.S. Pat. No. 4,644,059 and the period for culturing is typically based on arbitrary parameters, such as time or optical density, see e.g. U.S. Pat. No. 4,220,717. In this way, it is not possible to compensate for changes in culture conditions and suboptimal yields of polysaccharide are the inevitable result. In addition, harsh chemicals such as phenol are used to recover the polysaccharide, see e.g. U.S. Pat. No. 4,695,624 and EP 0 528 635.

In order to contribute to the goal of the WHO (World Health Organization) and GAVI (Global Alliance for Vaccines and Immunization), to make Hib conjugate vaccine available for all children in the world and in order to give people in developing countries a chance to get access to Hib-technology, a relatively simple and easily up-scalable production process has to be developed, patented and licensed to these countries under reasonable terms. The vaccine produced should meet the relevant WHO requirements.

BRIEF DESCRIPTION OF THE DRAWING FIGURES

FIG. 1 $OD_{590}$, pH and polyribosyl ribitol phosphate (PRP) concentration during a test cultivation on a 40 l scale.

FIG. 2 Simple purification process of polyribosyl ribitol phosphate (PRP).

DETAILED DESCRIPTION

The present invention relates to a method for producing a polysaccharide and to the use of the polysaccharide for producing a pharmaceutical composition. The method for producing the polysaccharide comprises:

culturing an encapsulated bacterium in a suitable culture medium at a suitable pH and temperature adjusting the pH of the culture medium to a constant value with base or acid until adjustment with respectively base or acid is not possible anymore delay lysis of the cells, preferably by cooling to below the temperature used for culturing optionally, recovering the polysaccharide from the culture medium.

One of the advantages of the polysaccharide production method according to the invention is that capsular polysaccharides, i.e. capsular antigen extracted from a pathogenic bacterium, may be obtained in a high yield (about 200-400 mg/l) in a very short time. Further optimization of the medium and/or cultivation method (fed batch instead of batch) will of course result in a much higher polysaccharide concentration. Whereas state of the art methods for producing capsular polysaccharides require between about 16 and 18 hours of fermentation, in the method according to the present invention, fermentation may typically be completed, i.e. optimal moment for termination is reached, within in between about 6 and 14 hours, preferably it is completed within about 7, 8, 9, 10 or 11 hours. It typically will not take more than about 12 to 14 hours. Exact times will of course depend on the bacteria and strains used and may differ slightly depending on the "physical condition" of the bacteria. In this context, the "physical condition" of the bacteria refers amongst others to the quality of the inoculum and is reflected in e.g. the duration of the lag phase of the culture.

Other advantages of the method according to the present invention are that the method is straightforward, reproducible and cost-effective and gives optimal yields, even after a change in culture conditions. Furthermore, the bacteria are cultivated using a simple medium which does not contain components from animal origin, except for hemin. This yields a clean medium which is a big advantage, because the trend nowadays is to minimise transfer of animal disease, such as BSE, by using as much as possible media free from animal components.

Yet another advantage is that it is also very flexible in that as soon as the cooling is started, cell lysis is delayed and harvesting of the polysaccharide can be done at any convenient time, as long as it is started within about 24 hours, preferably within about 8, 10, 12, 14 or 16 hours, more preferably within about 2, 4 or 6 hours after starting the cooling. The skilled person will understand that the higher the temperature after cooling, the quicker the harvest will have to be started, for best results. In one embodiment, the harvest is started about 1.5 hours after lowering the temperature. The method is scaled-up without substantial problems especially because harvesting is based on a physical parameter (pH) and not on something arbitrary as e.g. the time or optical density (OD). Furthermore the method results in a very stable bulk polysaccharide that can be purified using a relatively simple process. The purification process is based on the concentrated supernatant, the amount of auxiliary materials is therefore minimal. The purification results in a purified polysaccharide that is stable for a long time and that passes all the WHO requirements.

Capsular polysaccharides can be extracted from any encapsulated bacterium, be it Gram negative or Gram positive. Non-limiting examples of bacteria, which may be used, are strains from *Streptococcus, Staphylococcus, Enterococcus, Bacillus, Corynebacterium, Listeria, Clostridium, Haemophilus, Pneumococcus, Neisseria* and *Escherichia*. Of particular interest to human beings are capsular polysaccharides from *Haemophilus influenzae, Streptococcus pneumoniae* and *Neisseria meningitidis*. Especially *Haemophilus influenzae* has been widely used, see e.g. Rosenberg et al. (1961) J. Biol. Chem. 236: 2845 and Zamenhof et al. (1953) J. Biol. Chem. 203:695. Any strain of *Haemophilus influenzae* type b (Hib) may be used. Examples of suitable strains include the reference Hib strain, Eagan and the strain A760705.

Methods for culturing these bacteria are well-known in the art, for example from Meritt et al. (2000) J Biotechnology 81: 189. In general, a suitable culture medium is based on amino acids and/or yeast extract or peptone, sodium chloride (NaCl) and glucose, supplemented with NAD and hemin and buffered using a phosphate buffer. Preferably, the medium should not contain components from animal origin except for hemin. A suitable pH is generally a pH between about 6 and 8, preferably about 6.5 and 7.5 or about 6.8 and 7.2. The culturing temperature is typically about 30-37° C., preferably between about 35 and 37° C.

According to the method of the present invention, the pH is kept constant at a desired value using either acid or base. Any base or acid which is conventionally used for adjusting the pH in cell cultures may be used. Suitable bases and acids include NaOH, preferably in a concentration of about 1-5 mol/l and HCl, preferably in concentrated form.

At certain moment, the pH cannot be adjusted anymore using the chosen acid or base, because the pH now shows a tendency to decrease or increase respectively. This moment roughly corresponds to late logarithmic phase (see also FIG. 1). The pH is monitored without further adjustment. The decrease or increase of pH will slow down after some time, usually about 2-4 hours after pH adjustments have been discontinued if cultivating at about 35° C. At lower temperatures, this will take longer. Just before the decrease or increase starts to slow down, which will be predictable from test runs (unlike e.g. optical density), fermentation is terminated and the culture broth is harvested. Fermentation is preferably terminated by cooling, since this has many advantages. In the first place, it does not involve the use of harsh chemicals, like formaldehyde, which can also be used for termination. Secondly, it is a very economical way of terminating growth, because it does not involve additional materials. Thirdly, it has the concomitant advantage that the chance of lysis is minimized during harvest. Since harvest is a process which is typically not completed within a few minutes, cooling gives you the flexibility and time to harvest under optimal circumstances and at the optimal moment. Harvesting earlier may lead to for example 50% lower polysaccharide yield, depending on the harvesting time (see for instance FIG. 1). Harvesting at a later time will contaminate the polysaccharide fraction, because cells will have lysed and all kind of cellular material will have ended up in the medium from which the polysaccharide will be isolated (see for instance FIG. 1). These cellular contaminations will complicate any further isolation and purification procedure of the polysaccharide.

In order to terminate the fermentation for harvesting, the temperature is preferably lowered to below 30° C., more preferably to below 25° C., most preferably to below 20° C. The actual harvest, i.e. emptying the fermentor, may start within minutes after the fermentation has been terminated, but the cooling makes the procedure very flexible and allows for a delay of several hours at the convenience of the harvesting person. There is no need to wait o/n, which is almost inevitable if formaldehyde is used for killing cells. In one embodiment, harvest is started at least 2 hours after fermentation has been terminated. In another embodiment, harvest is started at least 3, 4, 5 or 6 hours after growth has been terminated.

Harvesting is typically done by centrifugation, and is optionally followed by inactivation, concentration and preferably diafiltration of the supernatant. Centrifugation is preferably at a speed of about 3000-6000 rpm. Centrifugation is optionally followed by inactivation. Inactivation, which is done to kill any microbial life, may be performed using formaldehyde, preferably in an end concentration which does not exceed 0.1% (w/v) overnight at about 2 to 8° C. In one embodiment 0.04% w/w formaldehyde was used to inactivate the supernatant. The concentrated supernatant may be stored before recovery of the polysaccharide, preferably by freezing, most preferably by freezing at $\leq -20°$ C., where it will be stable for at least two years if produced according to the method of the invention. In one embodiment, it was stable for at least three years.

In one embodiment, polysaccharide production during fermentation was estimated using an ELISA and was typically between about 200 and 400 mg/l in the supernatant, and was of rather high relative molecular mass (700-800 kDa).

Polysaccharide Recovery

The polysaccharide may be recovered from the medium, usually from its supernatant, using state of the art techniques. The recovery may lead to a partially, substantially or completely purified polysaccharide. Preferably, it yields a product which contains more than 80%, 85%, 90% or 95% of the starting polysaccharide. However, fermentation according to the method of the invention also allows for a very simple recovery process, which may also be used in combination with state of the art polysaccharide production processes. This simple recovery and purification process is characterised by the fact that no harsh chemicals such as phenol are used. Moreover, there is no need for high-speed centrifugation or ultracentrifugation, or chromatography. This makes the purification economically attractive, because there is no need to invest in an (extra) high-speed centrifuge or ultracentrifuge or in expensive column material. The process comprises four simple precipitation steps, which do not have to be repeated several times, as is frequently the case in state of the art purification schemes and which each last maximally 24 hours. In one embodiment, precipitation is conveniently performed o/n, i.e. for 15-18 hours.

This simple recovery process comprises:

a) using a cationic detergent to precipitate the polysaccharide or part of the contaminants from the supernatant to obtain a first polysaccharide fraction;

b) using alcohol to precipitate the polysaccharide from the first polysaccharide fraction to obtain a second polysaccharide fraction;

c) subjecting the second polysaccharide fraction to an alcohol precipitation in the presence of an anionic detergent, whereby the alcohol is present in a concentration which is below the concentration at which the polysaccharide precipitates;

d) precipitating the polysaccharide from the soluble fraction using alcohol to obtain a polysaccharide precipitate;

e) dissolving the polysaccharide precipitate and subjecting it to concentration and diafiltration.

The cationic detergent in a) is preferably Cetavlon (hexadecyltrimethyl ammonium bromide), preferably in a final concentration of about 0.01-1% (w/v). The anionic detergent in c) is preferably sodium deoxycholate (DOC), preferably in a final concentration of about 0.1-1% (w/v). The alcohol which is used in the precipitation steps is preferably ethanol, preferably in a final concentration of about 60-74% (v/v) in b); of about 10-50% (v/v) in c); and of about 60-85% (v/v) in e). In each step, solids and fluids (also referred to as pellets and supernatants) are separated by any one or a combination of centrifugation, decanting and filtration. After the last alcohol precipitation, the pellet is preferably separated from the supernatant by decanting and not by centrifugation. In any step, pellet with precipitated polysaccharide may be dissolved in any convenient solvent or liquid, for example using water or 1 mol NaCl. This simplified recovery process which may be used for all types of polysaccharides is also part of the invention.

Preferably, the purification is performed using concentrated supernatant. The amount of detergent and/or ethanol needed is based on concentrate volume. The purified polysaccharide is then stable for at least two years at ≦−20° C. In one embodiment, the purified polysaccharide was stable for at least three years.

In one embodiment, the polysaccharide is recovered by a process comprising a 0.65% (w/v) Cetavlon precipitation, a 72% (v/v) ethanol precipitation, a 32% (v/v) ethanol precipitation in the presence of 0.5% (w/v) DOC and a 64% (v/v) ethanol precipitation, preferably after clarification.

In another embodiment, the polysaccharide is purified using a 0.04% (w/v) Cetavlon precipitation in a). The polysaccharide will then stay in the supernatant. The alcohol precipitation may be performed by adding alcohol directly to the supernatant. The rest of the process is as mentioned before.

In yet another embodiment, the recovery process comprises a 0.65% (w/v) Cetavlon precipitation as well as a 0.04% (w/v) Cetavlon precipitation. The 0.04% (w/v) Cetavlon precipitation may for example be used to further purify the polysaccharide obtained after the 64% (v/v) ethanol step.

The alcohol in c) may be added before or after addition of the detergent. Alternatively, it is added simultaneously, i.e. separately at the same time or as a mixture. Preferably, the alcohol is added after the detergent.

A combination of the fermentation and the recovery method of the invention allows for polysaccharide of high purity. For example, capsular polysaccharide from *Haemophilus influenzae* type b isolated according to this combination of methods of the invention meets all the VHO specifications of purified polysaccharide to be used for the production of conjugated Hib vaccine.

Preferably, the purified polysaccharide fraction contains at least 90% (w/w) polysaccharide, more preferably at least 94, 95 or 96% (w/w) polysaccharide, based on the dry weight. The endotoxin content is preferably less than 10 IU/microgram, more preferably less than 8, less than 5, less than 2 or less than 1 IU/microgram, most preferably, it is less than 0.5 or less than 0.2 IU/microgram polysaccharide fraction. The nucleic acid content is preferably less than 1% (w/w), more preferably less than 0.8 (w/w).

Vaccine Production

A polysaccharide which is produced using the method of the invention may be used to increase the ability of the human or animal immune system to fight infections. In particular, it may be used for the preparation of a pharmaceutical composition for administration to a human or animal subject. The polysaccharide or a conjugate thereof is preferably administered parenterally, e.g. by injection or infusion by intravenous, intraperitoneal, intramuscular, intraarterial or intralesional route. The polysaccharide or a conjugate thereof may be combined with a pharmaceutically acceptable medium or delivery vehicle by conventional techniques known in the art. Methods for preparing parenterally administrable compositions are well known in the art and described in more detail in various sources, including, for example, Remington's Pharmaceutical Sciences, Ed. AR Gennaro, 20th edition, 2000, Williams & Wilkins, PA, USA. The polysaccharide is preferably administered in a therapeutically effective dose, i.e. one that will increase the ability of the human or animal immune system to fight infections.

Preferably, it is used for the production of a vaccine, for example a polysaccharide conjugate vaccine. Methods for producing conjugate vaccines are known in the art and described in e.g. Ada et al (2003) Clin. Microbiol. Infect. 9(2): 79-85, Dick et al (1986) Contributions to Microbiology and Immunology, vol. 10: Conjugate Vaccines: 48-114, and Jennings et al (1994) Neoglycoconjugates: Preparation and Applications: 325-371. Although there are slight variations in the methods used for producing conjugate vaccines, production methods typically comprise:

activation of the polysaccharide and/or the protein carrier conjugation of the (activated) polysaccharide to the (activated) protein carrier optionally, purification of the polysaccharide-protein conjugate optionally, formulation of the polysaccharide-protein conjugate.

The polysaccharide can be sized down to a consistent molecular mass before conjugation, by using controlled depolymerization methods known in the art. Suitable depolymerization methods comprise oxidation of vicinal diols, ultra-sonication, and acid or alkaline hydrolysis. Alkaline hydrolysis can be effected conveniently in a buffer, in order to insure pH stability throughout the reaction. A suitable alkaline buffer is bicarbonate-carbonate buffer, 0.1 to 1 mol/l at pH above 9, preferably above pH 10. These depolymerization reactions can be conducted at room temperature, but preferably in the cold, such as 2 to 8° C., to minimize unwanted side reactions, and preferably under vigorous agitation.

The polysaccharide may be activated before conjugation or before sizing down by activation methods known in the art, such as for example by using a cyanylating reagent (Kohn et al (1986) Appl. Biochem. Biotechnol. 9: 285-305). Suitable cyanylating agents include cyanogen bromide (CNBr), 1-cyano-4-(dimethylamino)-pyridinium tetrafluoroborate (CDAP), N-cyano-N,N,N-triethylammonium tetrafluoroborate (CTEA), and p-nitrophenylcyanate (pNPC). Alternatively, terminal aldehyde groups may be formed on the polysaccharide via oxidative cleavage of vicinal diols and conjugation may then be effected by reductive amination with a suitable reducing reagent, such as sodium cyanoborohydride.

The protein carrier may also be activated before conjugation by activation methods known in the art, such as for example by using a halogenoalkylating reagent (Bernatowicz et al (1986) Anal. Biochem. 155(1): 95-102.). Such a suitable reagent is bromoacetic acid N-hydroxysuccinimide ester.

The polysaccharide may be conjugated to the protein carrier directly or after (further) activation via spacer or linker molecules, introduced either on the (activated) polysaccharide and/or the (activated) protein carrier. For example, after activation of the polysaccharide with a cyanylating agent, (di)amino or amino acid spacers, such as cystamine or glycine, can be introduced onto the polysaccharide. Some diamino spacers can be further reduced to generate free thiol groups (de Weers et al (1998) Bioconjugate Chem. 9(3): 309-315.). Another suitable spacer is adipic acid dihydrazide (ADH) (Chu et al (1983) Infect. Immun. 40(1): 245-256). Alternatively, these spacers can be introduced onto the protein carrier by an amidation reaction.

Removal of excess spacers can be effected by purification methods known in the art, such as gel permeation chromatography, differential precipitation, and diafiltration. A suitable diafiltration system makes use of the tangential flow filtration principle on microporous membranes. Buffered salt solutions have been shown to facilitate this purification process. A suitable solution is a phosphate buffer, about 0.01 to 0.2 mol/l, with sodium chloride or equivalent salt, about 0.5 to 3 mol/l. With such a method, a spacer such as ADH can be removed to contamination levels below about 0.05 to 0.5% (w/w) of the ADH bound to the polysaccharide. Such a decontamination can be monitored by the use of high performance gel permeation chromatography (HP-GPC), with a UV detector set to a low wavelength, such as about 210 to 230 nm. Quantitation of residual ADH is then done through the use of a standard calibration.

After introduction of spacers onto the polysaccharide, conjugation to the protein carrier can be effected by the mediation of a carbodiimide amidation reagent. A suitable amidation reagent is N-(3-dimethylaminopropyl)-N'-ethylcarbodiimide hydrochloride (EDC), which can be supplemented by N-hydroxysuccinimide (NHS) to facilitate the reaction. Alternatively, thioether bonds can be formed by condensation between a thiolated polysaccharide and a halogenoacetylated protein carrier, without the help of an additional reagent.

A carbodiimide-mediated conjugation reaction can take place at slightly acidic pH, typically pH 4 to 6, thereby insuring preferential amidation of hydrazide spacer groups over amino groups found on the protein carrier. In one embodiment, the conjugation reaction takes place in a suitable buffer, in order to insure pH stability throughout the reaction. This obviates the need to have access to or to invest in a pH meter equipped with automatic titrator in order to make regular acid additions. In a preferred embodiment, a buffer devoid of carboxylic groups which react with carbodiimides, thereby impairing the desired conjugation reaction, is used. For instance, a buffer may be used which is made up of 2-morpholinoethanesulfonic acid (MES), 0.05 to 0.2 mol/l, and sodium chloride, 0.2 to 1 mol/l, at pH 5.5 to 6.1. The conjugation reaction can be quenched by the addition of alkali or an alkaline buffer, which brings the pH of the reaction mixture to about pH 7 or above, thereby preventing or drastically slowing down further carbodiimide-mediated amidation. A suitable alkaline buffer is a phosphate buffer, about 0.1 to 0.4 mol/l, at pH 8 to 9, added in a sufficient amount to neutralize the reaction mixture to about pH 7.

Removal of unreacted polysaccharide and protein can be effected by purification methods known in the art, such as gel permeation chromatography, hydrophobic interaction chromatography, differential precipitation, and diafiltration. A suitable gel permeation chromatography system makes use of Sepharose CL-4B, Sephacryl S-500 HR (Amersham), or equivalent gel media, with a neutral buffered saline solution as eluent. A suitable hydrophobic interaction chromatography system makes use of Butyl, Octyl-, or Phenyl Sepharose 6 Fast Flow (Amersham), or equivalent gel media, with a neutral buffered ammonium sulfate solution as binding eluent. A suitable differential precipitation system makes use of concentrated ammonium sulfate solutions. Residual unreacted polysaccharide and protein can be detected and quantified by the use of high performance gel permeation chromatography (HP-GPC), with a UV detector set to 280 nm., and a differential refractive index detector. Residual unreacted polysaccharide can also be quantified by a specific colorimetric assay after precipitation of the conjugate.

The preparation of conjugates is also described in U.S. Pat. Nos. 4,356,170, 4,644,059, 4,673,574, 4,695,624, 4,902,506, 7,667,170, EP 0 161 188, EP 0 477 508 and EP 0 848 011.

The polysaccharide, which is preferably a polyribosyl ribitol phosphate (PRP), may be coupled to any protein carrier. Suitable protein carriers increase its immunogenicity and include immunogenic membrane proteins, viral protein subunits, synthetic polypeptides and other immunogenic proteins. Most preferably, the protein carrier is a toxoid. Well-known toxoids used in conjugate vaccines are tetanus toxoid and diphtheria toxoid.

The polysaccharide produced using the method of the invention may be used to produce a monovalent vaccine. A suitable example of a monovalent vaccine is a polysaccharide or a conjugate vaccine only against *Haemophilus influenzae* type b (Hib). Alternatively, the polysaccharide of the invention may be used to produce a multivalent vaccine. It may for example be used to produce a tetravalent vaccine, such as diphtheria-tetanus-polio-Hib or diphtheria-pertussis-tetanus-Hib, or a pentavalent vaccine, such as diphtheria-pertussis-tetanus-polio-Hib, or diphtheria-pertussis-tetanus-hepatitis B-Hib.

The vaccine may be formulated in any convenient way. For example, a monovalent Hib vaccine may be freeze-dried or in liquid form, with or without the addition of a stabilizer, such as lactose, or of an adjuvant, such as aluminum phosphate.

It will be clear to the skilled person that the production method according to the invention may also be used for polysaccharide production from other polysaccharide containing microorganisms.

EXAMPLES

Example 1

Growth test of *Haemophilus influenzae* type b

A *Haemophilus influenzae* type b strain (A760705) isolated in Amsterdam was cultivated using a 50 l bioreactor (working volume of 40 l) with a NOVO control system. This strain was identified as being a *Haemophilus influenzae* type b using commonly used tests, such as immune- and serotyping, and morphology testing. The bioreactor was first filled with the basal medium (compound 1 to 5 in Table 1 dissolved in 35.5 l) before being sterilized in situ for 20 minutes at 110° C. Just before inoculation the proper amount of stock solutions were added to the medium (see Table 2). The bioreactor was inoculated using 1 l pre-culture, cultivated on a 3.5 l scale using the same medium and a frozen −70° C. seed lot of the Hib strain.

The pH was kept constant at 7.0 using 5 mol/l NaOH. The temperature was kept constant at 35° C. The dissolved oxygen (DO) was kept constant at 30% using air and oxygen through the headspace using a gas flow of 5 l/min. The stirrer speed was increased gradually from 300 to 700 rpm.

Different samples were taken using an auto sampler. The cultivation was monitored by measuring the optical density at 590 nm ($OD_{590}$), pH and PRP concentration (see FIG. 1). To monitor lysis of the culture a gram stain of a number of samples was controlled.

First the PRP concentration increased to around 320 mg/l, which was less or more parallel to the growth. The pH started to increase after about 7 hours cultivation, the $OD_{590}$ was at its optimal and was equal to 6.88. After about 12 hours cultivation the PRP was less or more constant at 330 mg/l while the pH increased further, the $OD_{590}$ decreased further and the lysis of the cells started slowly. After 16 hours cultivation the cells were not yet totally lyzed and the pH was equal to 7.92.

TABLE 1

Medium composition

| No. | Compound | Concentration (g/l) |
|---|---|---|
| 1 | L-Glutamic acid | 1.3 |
| 2 | $Na_2HPO_4 \cdot 2H_2O$ | 2.5 |
| 3 | KCl | 0.09 |
| 4 | NaCl | 6 |
| 5 | $NH_4Cl$ | 1.25 |
| 6 | Yeast extract (only low molecular mass fraction <30 kDa) | 10 |
| 7 | Cystine | 0.015 |
| 8 | $MgSO_4 \cdot 7H_2O$ | 0.6 |
| 9 | Dextrose | 5 |
| 10 | Hemin | 0.005 |
| 11 | NAD | 0.002 |

Notes:
compounds 1 to 5 can be dissolved in water, autoclaved after adjusting the pH to 7.5 and stored (basal medium). Compound 6 to 11 are stored separately (following Table 2).

After a couple more hours at room temperature, total lysis of the cells was noticed, the pH was equal to 8.43 and the $OD_{590}$ to 4.08. The PRP concentration was equal to 480 mg/l, because of the total lysis.

TABLE 2

Stock solutions for production medium

| Stock | Compound | Medium (g/l) | Stock (g/l) | ml stock/l |
|---|---|---|---|---|
| 1 | 6: Yeast extract | 10 | 120 | 83.33 |
| 2 | 7: Cystine | 0.015 | 0.6 | 25 |
|  | 8: $MgSO_4 \cdot 7H_2O$ | 0.6 | 24 |  |
|  | 9: Dextrose | 5 | 200 |  |
| 3 | 10: Hemin | 0.005 | 1 | 5 |
| 4 | 11: NAD | 0.002 | 0.4 | 5 |

This experiment was meant to monitor Hib cultivation, the supernatant was not purified according to the process described above.

The optimal harvest time of this culture was after around 10 hours cultivation. To postpone lysis, the culture could have been cooled down to a temperature lower than the cultivation temperature, and some more PRP could have been secreted during cooling. Harvesting at the exponential phase would have meant a low PRP yield.

Example 2

Production of Polyribosyl Ribitol Phosphate (PRP)

PRP was produced under the conditions of Example 1 on a 350 l scale. The cultivation was not continued till all the cells were lyzed but was stopped after 8.3 hours at a pH of 7.43 and an $OD_{590}$ of 4.4 by starting the cooling using tap water through the bioreactor jacket. The culture was harvested 1.5 hours later using a continuous centrifuge. At the start of the harvest the PRP concentration in the supernatant was equal to 277-377 mg/l, and the temperature of the culture was equal to 19° C. The supernatant was inactivated by adding a 2.7 mol/l formaldehyde solution to the supernatant till a concentration of about 0.1% (v/v). The supernatant was concentrated to about 9.6 l and diafiltrated using PBS. The concentrated supernatant was stored at $\leq -20°$ C.

Example 3

Purification of Polyribosyl Ribitol Phosphate (PRP)

1.5 l concentrated supernatant from Example 2 was purified using the process in FIG. 2 four months after the cultivation.

After purification, 12 flasks containing each 30 ml liquid pure PRP were freeze-dried to determine the purity based on dry mass (WHO TRS 814 Annex 1 1991 and TRS 897 Annex 1, 2000).

All the samples (liquid and freeze-dried, including IPC samples) were analyzed for PRP, nucleic acids and protein content. Purified PRP was also analyzed using HP-GPC (Hennessey et al (1993) J. Liq. Chromatogr. 16(8): 1715-1729), NMR (Lemercinier et al (2000) Biologicals 28(3): 175-183), and UV spectroscopy. Determination of ribose (orcinol reaction: Ashwell et al (1957) Meth. Enzymol. III: 73-105), phosphorus (Ames et al (1966) Meth. Enzymol. VIII: 115-118), and residual protein (Lowry et al (1951) J. Biol. Chem. 193: 265-275), was done by colorimetric assays. Endotoxin was measured with the LAL assay.

See Table 3 for the composition of purified PRP. The PRP had a relative molecular mass of 765 kDa. The PRP met all the WHO specifications of purified polysaccharide to be used for the production of conjugated Hib vaccines. The purification yield based on the orcinol assay was equal to 80%. The DOC concentration in the end product was lower than 5 μg/ml (detection limit) and the formaldehyde lower than 0.005 nmol/l.

TABLE 3

Composition of purified PRP

| Component | PRP composition | WHO specifications |
|---|---|---|
| Total mass (g); 100% | 7.39 | — |
| Dry mass (%) | 98.62 | — |
| PRP (%) | 96.81 | — |
| Phosphorus (%) | 7.84 | 6.8-9 |
| Pentose (%) | 35.22 | 32-38 |
| Nucleic acids (%) | 0.75 | <1 |
| Protein (%) | 0.33 | <1 |
| Endotoxin (IU/μg) | 0.11 | <10 |

IU = International Units

Example 4

Activation of Polyribosyl Ribitol Phosphate (PRP)

PRP (1.023 g; endotoxin: 0.02 IU per μg PRP) was concentrated to ~10 g/l with the help of a tangential flow filtration system, equipped with a 100 kDa molecular weight cut off (MWCO) filter cartridge. Recovery: 999 mg (98%). The PRP concentrate was then transferred to a jacketed vessel, and cooled down to ~4° C. An equal volume of pre-chilled sodium bicarbonate/carbonate buffer (0.4 mol/l, pH 10.5) was then added rapidly, and the resulting reaction mixture maintained at ~4 ° C under vigorous agitation (~400 rpm) for 90 min. Decrease of the average relative molecular mass ($M_r$) of PRP was monitored by HP-GPC.

At the end of this alkaline degradation step, CNBr (5 mol/l in acetonitrile) was added (2.2 ml per g PRP). The previous conditions were maintained for another 10 min. Thereafter, three volumes of pre-chilled ADH (18 g per g PRP) reagent, 30 g/l in bicarbonate solution (1 mol/l), were rapidly added. The previous conditions were maintained for another ~16 h (at pH ~9).

The activated PRP(PRP-ADH) was then concentrated to ~20 g/l, with the TFF system, equipped with a 10 kDa MWCO filter cartridge. Extensive diafiltration then took place to remove the excess of reagents, principally ADH. The first step made use of ~20 volumes sodium phosphate buffer (0.1 mol/l, pH 7.2; with NaCl, 1.5 mol/l). The progress of the removal of excess ADH was followed by HP-GPC at 215 nm, relative to a standard calibration curve. When excess ADH was below 0.05% (w/w) of total ADH, diafiltration continued with ~5 volumes MES buffer (0.1 mol/l, pH 6.1; with NaCl, 0.5 mol/l). PRP-ADH was then concentrated to an estimated concentration of ~25 g/l. The concentrated PRP-ADH was analyzed for ribose and amino groups (TNBS reaction: Habeeb et al (1966) Anal. Biochem. 14: 328-336), and stored at 2 to 8° C. Recovery: 764 mg (75%). Activation ratio: 25 PRP repeat units (RU) per ADH group, or 1.9% (w/w) ADH.

Example 5

Conjugation of Activated Polyribosyl Ribitol Phosphate (PRP-ADR) to Tetanus Toxoid (TTd)

Tetanus toxoid (TTd; 1.327 g; 1,623 Lf/mg PN; 1,900 Lf/ml) was concentrated to ~20 g/l, with the TFF system (10 kDa MWCO filter cartridge). Diafiltration then took place, in part to remove excess medium components, with ~5 volumes MES buffer (pH 6.1). TTd was then concentrated to an estimated concentration of ~30 g/l. The concentrated TTd was analyzed for protein content (Lowry reaction), and stored at 2 to 8° C. Recovery: 1.186 g (89%).

PRP-ADH concentrate (707 mg) was then transferred to a jacketed reactor, and cooled down to ~4° C. TTd concentrate (786 mg) was then added, and the resulting mixture brought down to ~4° C., under gentle agitation (~200 rpm), to prevent foaming. Pre-chilled EDC reagent, 100 g/l in MES buffer (pH 6.1), was then added (1 g per g TTd). Finally, MES buffer (pH 6.1) was added to complete to the total volume. This reaction mixture (PRP/TTd ratio of 0.93 w/w) was maintained at ~4° C., under gentle agitation. The reaction was stopped at 3 h 30, when the residual TTd level reached 4.4%, as measured by HP-GPC at 280 nm. The reaction was quenched by the addition of an equal volume of sodium phosphate buffer (0.1 mol/l, pH 8.0; with EDTA, 0.005 mol/l), and then stored at 2 to 8° C.

Example 6

Purification of Polysaccharide-Protein Conjugate

The conjugation mixture was clarified on a 0.45 μm in-line filter unit. It was then purified in five equal portions on a GPC column (4.4 cm diameter, 45 cm packed bed height), packed with Sepharose CL-4B (Amersham Pharmacia Biotech), and eluted with sodium phosphate buffer (0.1 mol/l, pH 7.0; with EDTA, 0.005 mol/l) at a flow rate of 6 ml/min. Elution was monitored with differential refractive index, UV (226 nm), and conductivity detectors. Fractions were collected every 2 min for ~0.9 CV. The fractions of the first run were then analyzed for ribose, and protein content (BCA reaction: Smith et al (1985) Anal. Biochem. 150(1): 76-85), and stored at 2 to 8° C. Fractions corresponding to the first peak containing ribose (187 mg PRP) and protein (440 mg TTd), and having an homogeneous PRP/TTd ratio (0.43 w/w), were pooled from all runs (pool 1): this is the high $M_r$, conjugate pool used later for vaccine preparation. Remaining fractions primarily comprising unconjugated PRP, were also pooled (pool 2) to calculate the mass balance: this pool contains medium and low $M_r$, conjugate, free (i.e. unconjugated) PRP-ADH, and free TTd. The mass balance was: 78% PRP, and 76% TTd, based on conjugation starting materials amounts (see Table 4). The high $M_r$, conjugate pool (pool 1) was then concentrated to ~4 g/l, with the TFF system (10 kDa MWCO filter cartridge). Diafiltration then took place, with ~10 volumes Tris buffer (0.02 mol/l; pH 7.0). The buffer-exchanged conjugate (PRPTTd) was then concentrated to ~1 g/l, and sterilized by filtration on a 0.22 μm in-line filter unit. The sterile concentrated PRPTTd bulk was then analyzed by HP-GPC, and for ribose, and protein content (BCA reaction), and then stored at 2 to 8° C. Recovery: 170 mg PRP (22%), and 372 mg TTd (45%). The final PRP/TTd ratio was 0.46 (w/w) (WHO specification: 0.3-0.6) and the endotoxin content 6.58 IU per μg PRP. Analysis of free PRP (Guo et al (1998) Biologicals 26(1): 33-38) gave 12.7% (WHO specification: <20%). The stability of the sterile concentrated PRPTTd bulk was then studied for a total of six months while stored at 2 to 8° C.

TABLE 4

Recoveries and mass balance of PRPTTd

| | PRP | | TTd | | PRP/TTd | WHO specification |
|---|---|---|---|---|---|---|
| | (mg) | (%) | (mg) | (%) | (w/w) | (w/w) |
| Initial mix | 768 | 100 | 829 | 100 | 0.93 | — |
| GPC pool 1 | 187 | 24 | 440 | 53 | 0.43 | — |
| GPC pool 2 | 415 | 54 | 188 | 23 | — | — |
| Mass balance | 602 | 78 | 628 | 76 | — | — |
| Sterile final bulk | 170 | 22 | 372 | 45 | 0.46 | 0.3-0.6 |

Notes:
relative molecular masses ($M_r$) were determined against pure pullulan standards on OHpak (Shodex) SB-805 and SB-804 HP-GPC columns.
Detection: differential refractive index, and UV (215, and 280 nm). $M_r$ calculations based on the UV 280 nm signal.

Example 7

Formulation of Polysaccharide-Protein Conjugate to a Monovalent Hib-Vaccine

In another experiment, sterile concentrated PRPTTd bulk (121 mg PRP; 348 mg TTd; PRP/TTd ratio of 0.35 w/w; 1.9% free PRP, endotoxin 7.27 IU per µg PRP) was formulated with Tris buffer and sucrose, in preparation for lyophilization. The bulk vaccine was first diluted with Tris buffer (0.1 mol/l; pH 7.0), sucrose was then added (0.5 mol/l), and water for injection added to complete to the total volume. Portions of 1.4 ml were transferred to multiple dose vaccine vials, and lyophilization then took place. Due to losses inherent to the automatic filling process, ~1,500 multiple dose vials were finally obtained, for a total of 7,500 injectable doses (i.e. 5 per vial). Each vial contained 8-12 µg PRP per ml human dose, to be reconstituted with NaCl solution. The stability of the lyophilized PRPTTd vaccine was then studied for 18 months (planned for a total of 36 months), at normal room temperature, and under stress conditions at 37° C. (see Table 5). Glass transition temperature (measured by DSC) remained high at about 63° C., and remained constant, showing that the lyophilized vaccine was in a stable physical state. For the determination of free PRP, sucrose had to be first removed by buffer exchange, using centrifugal ultrafiltration devices (10 kDa MWCO). The stability of the sterile concentrated PRPTTd bulk was also studied for a total of six months (see Table 5). During these studies, $M_r$ remained constant, and no significant increase of free PRP was observed.

TABLE 5

Stability of PRPTTd

| | $M_r$ (kDa) | Free PRP (%) | Glass transition (° C.) | pH |
|---|---|---|---|---|
| Sterile final bulk | | | | |
| t = 0 | 1,463 | 1.9 | — | 7.00 |
| t = 4 wk | n.a. | 1.8 | — | 7.00 |
| t = 24 wk | 1,439 | 2.7 | — | 6.90 |
| Lyophilized vaccine | | | | |
| t = 0 | 1,381 | 10.1 | 64 | 6.56 |
| t = 3 mo. | 1,325 | n.a. | — | — |
| t = 6 mo. | 1,396 | 5.5 | — | — |
| t = 12 mo. | 1,306 | 6.3 | — | — |
| t = 18 mo. | 1,334 | 5.7 | — | — |
| Stress study (37° C.) (lyophilized vaccine) | | | | |
| t = 1 wk | 1,337 | 6.9 | 63 | — |
| t = 4 wk | 1,337 | 4.1 | 63 | — |
| WHO specification | | <20 | — | — |

Notes:
free PRP determination in lyophilized vaccine is possible only after removal of excess sucrose by buffer exchange. High values (>10%) are due, in part, to residual sucrose, which interferes with the orcinol assay for ribose. $M_r$ calculations: see Table 4. The glass transition was measured using differential scanning calorimetry (DSC).

The invention claimed is:

1. A method for recovering a polysaccharide from a fermentation broth, comprising:
   employing a cationic detergent to precipitate the polysaccharide or part of the contaminants from the supernatant to obtain a first polysaccharide fraction;
   employing alcohol to precipitate the polysaccharide from the first polysaccharide fraction to obtain a second polysaccharide fraction;
   subjecting the second polysaccharide fraction to an alcohol precipitation in the presence of an anionic detergent, whereby the alcohol is present in a concentration which is below a concentration at which the polysaccharide precipitates;
   precipitating the polysaccharide from the soluble fraction employing alcohol to obtain a polysaccharide precipitate; and
   dissolving the polysaccharide precipitate and subjecting it to concentration and diafiltration.

2. The method according to claim 1, wherein the anionic detergent comprises sodium deoxycholate.

3. The method according to claim 1, wherein the anionic detergent has a final concentration of about 0.1-1% w/v.

4. The method according to claim 1, wherein the alcohol comprises ethanol.

5. The method according to claim 1, wherein the alcohol during the step of employing alcohol to precipitate the polysaccharide from the first polysaccharide fraction to obtain a second polysaccharide fraction has a final concentration of about 60-74% v/v.

6. The method according to claim 1, wherein the alcohol during the step subjecting the second polysaccharide fraction to an alcohol precipitation in the presence of an anionic detergent has a final concentration of about 10-50% v/v.

7. The method according to claim 1, wherein the alcohol employed during the step of precipitation of the polysaccharide from the soluble fraction has a final concentration of about 60-85% v/v.

8. The method according to claim 1, wherein the cationic surfactant comprises hexadecyltrimethyl ammonium bromide.

9. The method according to claim 1, wherein the polysaccharide is obtained from *Haemophilus influenza* type b.

\* \* \* \* \*